United States Patent [19]
Waynant

[11] Patent Number: 5,474,089
[45] Date of Patent: Dec. 12, 1995

[54] METHOD AND DEVICE FOR REVERSIBLE STERILIZATION

[75] Inventor: Ronald W. Waynant, Laurel, Md.

[73] Assignee: The United States of America as represented by the Secretary of the Department of Health and Human Services, Washington, D.C.

[21] Appl. No.: 721,784

[22] Filed: Jun. 26, 1991

[51] Int. Cl.⁶ .................................................. A61B 19/00
[52] U.S. Cl. ........................................ 128/843; 128/842
[58] Field of Search ................................. 128/842, 843, 128/917, 918, 830, 831, 832, 834, 837, 838, 839, 840

[56] References Cited

U.S. PATENT DOCUMENTS

| | | | |
|---|---|---|---|
| 3,422,813 | 1/1969 | Braley, Jr. et al. | 128/843 |
| 3,699,957 | 10/1972 | Robinson | 128/843 |
| 3,704,704 | 12/1972 | Gonzales . | |
| 3,777,737 | 12/1973 | Bucalo . | |
| 3,828,764 | 8/1974 | Jones | 128/843 |
| 3,918,431 | 11/1975 | Sinnreich . | |
| 4,013,063 | 3/1977 | Bucalo | 128/843 |
| 4,350,806 | 9/1982 | Wagener . | |
| 4,365,621 | 12/1982 | Brundin | 128/843 X |
| 4,377,010 | 3/1983 | Fydelor et al. . | |
| 4,682,592 | 7/1987 | Thorsgard . | |

FOREIGN PATENT DOCUMENTS 8303751 11/1983 WIPO .................................. 128/843

OTHER PUBLICATIONS

"Laser Recanalizaion of Occluded Atherosclerotic Arteries In Vivo and In Vitro", G. A. Abela, et al. Laboratory Investigation, Coronary Artery Disease, Circulation 71, No. 2, 403–411, 1985.

*Primary Examiner*—Sam Rimell
*Attorney, Agent, or Firm*—Lowe, Price, Leblanc & Becker

[57] ABSTRACT

A blocking device is non-surgically inserted in a duct of a reproductive system of either a male or female subject. The device may be in the form of a stent including an expandable section for sealingly engaging the duct to effect sterilization by preventing passage of gametes therethrough. The stent preferably includes a predetermined portion which is ablatable by application of a known intensity of laser irradiation. When desired, a laser beam may be used to ablate the portion of the blocking device in order to reopen the duct and to re-establish fertility of the subject. One embodiment of the device includes a guiding segment for guiding a fiber optic device to a position adjacent the ablatable portion and for accurate application of the laser beam thereto, thereby reducing potential organic damage from a misdirected laser beam. In another embodiment, the stent includes a collapsible frame structure compressed by a spring, and a central ablatable blocking portion. Upon release of the spring, the frame expands to engage the duct.

18 Claims, 2 Drawing Sheets

METHOD AND DEVICE FOR REVERSIBLE STERILIZATION

TECHNICAL FIELD

This invention relates to sterilization devices, and more particularly to a relatively permanent male and female sterilization device which is reversible in effect. Still more specifically, the invention relates to simply structured and nonsurgically implantable sterilization devices, which require minimal nonsurgical intervention for reversal of the sterilization effects thereof.

BACKGROUND ART

Numerous techniques and devices are known and available for sterilization of males or of females. Such techniques are frequently irreversible or, when reversal is surgically attempted, are not always successful in re-establishing flow of sperm through reconnected male ducts or passage of ova through reconnected female ducts. Moreover, where sterilization devices are surgically implanted, severance of the vas deferens (or other) duct of a male or of the fallopian tubes of a female is required. Reversal of sterilization effected by such devices may also require surgery. Difficulties and uncertainty are thus also encountered in re-establishment of fertility where known sterilization devices are used.

For example, U.S. Pat. No. 3,704,704 discloses a valve which may be surgically inserted within either the fallopian tubes of the female of the vas deferens of the male. Rather than permanently preventing conception by cutting (and/or tying) the vas deferens or the fallopian tubes, the disclosed valve spool is inserted in the cut duct. The valve spool may be completely closed to preclude passage of either sperm or ova through the respective tube, or may be opened by movement of a rotary element which is selectively movable to either the closed or open position.

However, in addition to the requirement for surgery to implement sterilization by cutting of the appropriate duct, reversal of the sterilization condition is effected by a surgical incision and insertion of a special tool to implement rotation of a rotatable element in the valve spool. Alternatively, external magnetic fields are contemplated for rotating a magnetically polarized element in the valve spool, coupled with X-ray verification. Thus, the patient is required to undergo at least one, possibly two, surgical procedures, along with exposure to external magnetic fields as well as to X-ray irradiation.

Another valved sterilization device, disclosed for use with the male vas deferens, is described in U.S. Pat. No. 3,777,737, wherein the vas deferens is at least partly cut transversely to form two separated sections with a ring barrier therebetween. The device includes a valve inserted between the separated portions of the duct, thus to prevent communication therebetween. The valve is inserted in the open position and, upon healing of the vas, is closed from the exterior of the body. Both closure of the valve and subsequent reopening, if desired, are effected by application of an exterior magnetic force to act upon an elongated bar magnet section of the valve.

Such devices are clearly susceptible to unintended effects of external stray magnetic fields, whether caused by geographical conditions or by modern technological devices such as magnetic resonance imagers. Accordingly, neither the sterilization effects nor the reversal thereof may be relied upon with complete assurance.

Other reversible sterilization devices are known which do not rely on magnetic fields for activation. For example, U.S. Pat. No. 4,682,592 teaches a reversible male sterilization device including a compressive plug, connected by a spring-like handle through an elongated tube and plunger to the external environment. The plug, which may be of rubber, foam or other compressible material which may expand under the effects of heat or moisture, is inserted to a proper position by a physician who then activates the plunger, withdraws the tube and disconnects a retrieval line from a hook on the plunger. Alternatively, an inflatable plastic cap is provided at the end of a valved hollow tube which fits within the male urethra. The tube is inserted by the user and a fluid injected to inflate the plastic cap thus to block the appropriate duct. After intercourse the device is removed from the urethra. Sterilization effected by the device is thus not reversible unless the device is withdrawn. Moreover, the complexity of the procedure appears likely to discourage widespread use thereof.

U.S. Pat. No. 3,918,431 discloses a surgical device for obturating fallopian tubes of a female to effect temporary sterilization. The device is positioned through the cervix using an endoscope and pneumatic insufflating means. A removable plug member is included to permit normal ovulation. The plug may be removed to uncover an opening establishing communication through the fallopian tube and thus to permit normal ovulation. At any time, the plug may be replaced, as desired. However, the disclosed plug element includes a magnetized hard metallic insert surrounded by a synthetic resinous sheath, serving as a tool retention means. Thus, although not relying on magnetic fields for operation, effectiveness of the disclosed device may be susceptible thereto.

The above described valve and plug devices require interaction among a plurality of components, including portions which are relatively movable with respect to one another. Thus, to attain reliable blockage of the ducts it is necessary to provide closely matched dimensional tolerances among the various components, whether movable or stationary. The resultant complexity of the known reversible sterilization devices accordingly increases the costs associated therewith and makes the same unaffordable precisely to individuals who, for economic circumstances, may wish to use sterilization devices. Accordingly, the difficulty and expense, as well as the discomfort and surgical risk, associated with implantation of prior art devices or with execution of known techniques frequently acts as a deterrent to sterilization.

Inasmuch as reversal of the sterilization effects of the above described devices or procedures, if at all possible, requires undergoing a surgical procedure, patients who contemplate subsequent childbearing are frequently deterred from undergoing sterilization. Instead, such patients rely on less effective devices for achieving birth control, such as interuterine devices, birth control pills, condoms and the like. However, such birth control devices are not as effective for preventing of conception and pregnancy as is complete sterilization.

There is thus a need in the prior art for a simple and inexpensive device for use in a reliable and effective nonsurgical method for effecting reversible sterilization of males or females.

DISCLOSURE OF INVENTION

It is accordingly an object of the present invention to provide a simple device, which may be used with male or female subjects, for reliably sterilizing the subjects and for reliably reversing the sterilizing thereof.

It is still another object of the invention to provide a method for reliably sterilizing and for reliably reversing sterilization of a male or female subject, in a manner relatively immune to the effects of external fields.

It is yet a further object of the invention to provide a method for sterilizing a male or a female subject by insertion of a stent or similar device into a duct in the reproductive system of the subject.

It is a more particular object of the invention to provide a method for reversing a sterilization procedure by inserting a known fiber optic device in a duct of the reproductive system, positioning the fiber optic device to guide laser radiation to a predetermined ablatable portion of a previously implanted device which is blocking the duct, exciting a laser externally of the subject, and applying the laser radiation to the fiber optic device for ablating the predetermined portion of the previously implanted device thereby to reopen the duct.

It is a more particular object of the invention to provide a simplified structure which is easily fabricated and easily inserted in a non-surgical procedure for reliably effecting sterilization of a male or female subject.

It is yet a further object of the invention to provide a reversible sterilization device which is relatively immune to effects of external fields.

It is a more specific object of the invention to provide a sterilization device for blockage of a duct in males or females, including a portion structured for laser ablation to reverse the sterilization.

In accordance with these and other objects of the invention, there is provided an improved method for reversible sterilization of a subject, including the steps of inserting a blocking member into a duct in a reproductive system of the subject thereby to block the duct and changing dimensions of an engaging element of the blocking member, thereby to engage the duct and to seal the blocking member in the duct.

The step of changing dimensions may include enlarging an outer dimension of the engaging element in order to engage an inner surface of the duct.

The inserting step may include insertion of a stent having the blocking member centrally located therein and having the engaging element at a peripheral portion thereof. For such a stent, the step of changing dimensions may include the further steps of endoscopically inserting a balloon structure at a distal end of a catheter to a vicinity of the engaging element, together with enlarging the balloon structure to contact and enlarge the engaging element, thereby to cause the engaging element to expand and sealingly engage an inner surface of the duct.

Alternatively, the inserting step may include insertion of a compressed stent having the blocking member centrally located therein and having the engaging element at a peripheral portion thereof. For such a compressed stent, the step of changing dimensions may include the step of releasing a spring compressing the stent, thereby enlarging the peripherally located engaging element to contact and sealingly engage an inner surface of the duct.

Reversal of the sterilization effected by the blocking device is preferably implemented by inserting an optical device into the duct and applying laser radiation to the optical device thereby to ablate a predetermined ablatable portion of the blocking member and to unblock the duct.

Preferably, the optical device is a fiber optic device which is inserted to be in a predetermined position relative to the ablatable portion of the blocking member. Laser radiation of a predetermined intensity is applied to the fiber optic device externally of the duct and is guided by the fiber optic device to the ablatable portion of the blocking device.

In accordance with another aspect of the invention, there is provided a reversible blocking device for a duct in a reproductive system. The blocking device includes a seating portion for seating the device in the duct and a blocking section for blocking passage of reproductive gametes therethrough. The blocking section includes an ablatable portion having a predetermined thickness for unblocking the duct by application of an ablating laser beam thereto.

Preferably, the reversible blocking device includes a stent which includes the seating portion at a peripheral portion thereof. The ablatable portion of the blocking section is mounted to the seating portion and is located substantially at a central portion of the stent.

In such a stent, the seating portion includes a flexible portion adapted to be flexibly enlarged by application of pressure thereto and a structure capable of engaging an inner surface of the duct. The stent further includes a guide section connecting the ablatable portion to the seating portion for guiding a distal end of a catheter to contact the ablatable portion to apply the ablating laser beam thereto.

In an alternate embodiment of the stent, the seating portion includes a coiled annular element adapted to be flexibly enlarged by application of spring pressure thereto. The stent further includes a spring for releasably compressing the annular element of the stent during insertion in the duct. The spring engages the annular element and, upon release of the spring, the annular element of the stent is enlarged to engage the duct.

The foregoing and other objects, features and advantages of the present invention will become readily apparent to those skilled in the art from the following description wherein there is shown and described preferred embodiments of the invention, simply by way of illustration and not of limitation of the best mode (and alternative embodiments) for carrying out the invention. The invention itself is set forth in the claims appended hereto. As will be realized upon examination of the specification with due reference to the drawings, the present invention is capable of still other, different, embodiments and its several details are capable of modifications in various obvious aspects, all without departing from the invention which is recited in the claims. Accordingly, the drawings and the descriptions provided herein are to be regarded as illustrative in nature and not as restrictive of the invention.

BRIEF DESCRIPTION OF THE DRAWINGS

The accompanying drawings, incorporated into and forming a part of the specification, illustrate several aspects of a preferred embodiment of the present invention and, together with the description, serve to explain the principles of the invention. In the drawings.

BEST MODE FOR CARRYING OUT THE INVENTION

Figure 1:
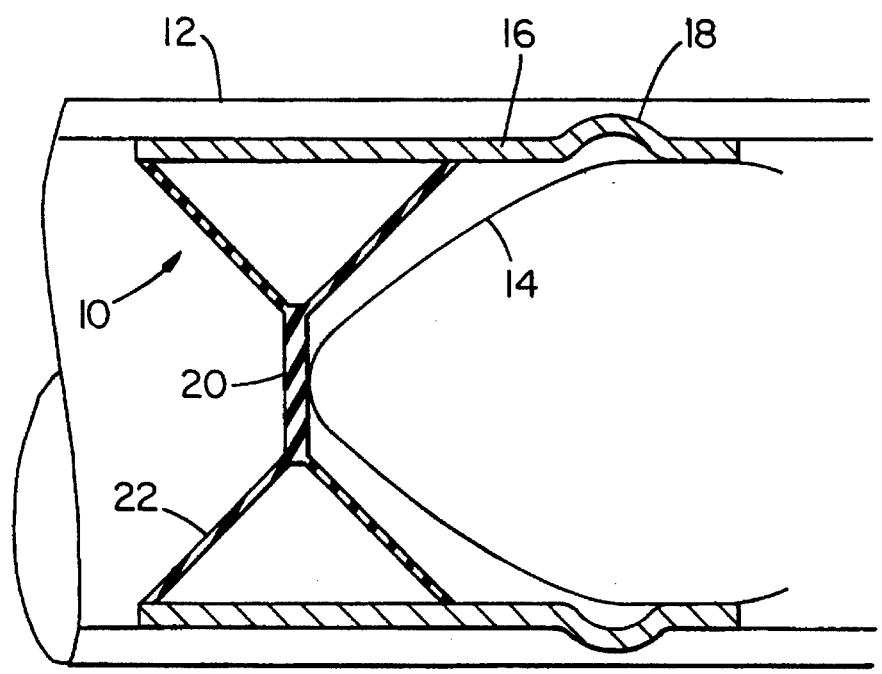
FIG. 1 is a cross sectional view illustrating one embodiment of the inventive device seated in a duct together with an insertion tool therefor.

Referring now to the embodiment of the invention illustrated in FIG. 1, there is illustrated at FIG. 1 one embodiment of the inventive device seated in a duct and effecting blockage thereof. More specifically, in accordance with the invention there is provided a stent 10 for blocking passage of human gametes through a duct or tube 12.

Inasmuch as the invention may be used for sterilization of either males or females, duct 12 may be the vas deferens of a male or a fallopian tube of a female. Moreover, it should be appreciated that the inventive concept may also be applied to reversible blocking of ducts or tubes other than those found in the reproductive systems of humans.

The function of a stent is to distend, expand, or open a passageway to permit materials to pass therethrough. Stents are used in conjunction with coronary angioplasty, for example, to engage the inner surface of a coronary artery (or other blood vessel) after expansion of a balloon structure therein in order to prevent collapse of the artery after withdrawal of the balloon therefrom. Of necessity, such known stents are open structures in order to permit blood flow therethrough.

Techniques for construction, insertion and engagement of stents, as well as the structural composition thereof, have thus been developed and are known to those of ordinary skill in the art.

In the present invention, it is contemplated that stent 10 be positioned at an appropriate location in the reproductive system by endoscopic means, such as by use of a catheter having an inflatable balloon at a distal end thereof. Such a balloon is symbolically illustrated at 14 in FIG. 1.

Stent 10 includes a seating element 16 for fixedly seating the stent at the selected location in duct 12. Seating element 16 is located at a peripheral portion of stent 10, and includes a specific engaging structure 18 for sealingly engaging duct 12. Preferably, engaging structure 18 is sufficiently flexible to be expanded by balloon 14 upon inflation thereof. Accordingly, in the illustration of the first embodiment of the invention seating element 16 is shown as being made of metal or similar material. Of course, if a metal is used then the metal is preferably coated with a known biocompatible material, such as a biocompatible polymer, to eliminate toxicity of the device and to avoid any reaction with the duct 12 or with biological products travelling therein. Indeed, the entire stent (including seating element 16) is preferably formed of or coated with a biocompatible polymer. Such polymers are known in the art, as illustrated by the disclosures of U.S. Pat. Nos. 4,350,806 and 4,377,010.

Thus, in accordance with the invention a balloon catheter or other device may be used to insert a stent 10 via natural ducts, without requiring any surgical incision. Upon expansion of the balloon, the diameter of the seating element, and specifically of the engaging structure 18, is permanently (or semi-permanently) increased thus seating the stent device in duct 12. Once stent 10 is seated, balloon 14 is deflated and withdrawn.

Accordingly, use of materials with at least semi-permanent deformation characteristics, such as polymer coated metals, is advantageous in properly positioning the device. Indeed, paralene has been used to coat implantable electronic devices, penile implants and the like. Such a material may be advantageously used with the present invention.

As is also clear from FIG. 1, the inventive sterilization device includes a barrier 20, thus occluding duct 12 and preventing passage therethrough of biological material. In the primary use contemplated for the invention, duct 12 is in the reproductive system of the subject and barrier 20 thus blocks gametes, whether sperm or ova, from passage through the duct, thus effecting the desired sterilization.

The structure of the inventive stent 10 provides the blocking barrier 20 at a central location of the stent, surrounded by an annular portion 22 having a triangular cross section. The triangular cross section of annular portion 22 thus provides a frustoconical structure to the stent when viewed in the longitudinal direction of the duct 12. Such a structure has a number of advantages associated with reversal of the sterilization effected by the stent.

It is a major advantage of the invention that the sterilization effected by the device may be reversed after implantation. In order to reverse the blockage of duct 12 by barrier 20, the stent is provided with an ablatable portion, e.g., barrier 20.

When the stent is formed of a stretchable material such as polyethylene or polystyrene, barrier 20 may have a thickness in the range of 0.1 mm to 3 mm, and preferably in the range of 0.5 mm to 1 mm. A layer having a thickness in the above described range may be ablated by application of a laser beam having an intensity on the order of 1 $J/cm^2$.

Structures for applying such beams are well known in the art, as illustrated by the publication "Laser Recanalization of Occluded Atherosclerotic Arteries in Vivo and in Vitro", George S. Abela, et al., *Circulation*, Vol. 71, No. 2, Feb. 1985, pp. 403–411. Indeed, ablation of polymer and either organic or inorganic materials is easily accomplished by laser radiation delivered through fibers. The technique can be accomplished by almost any high power, high energy laser of any wavelength. See "Excimer Laser Ablation and Thermal Coupling Efficiency to Polymer Films", P. E. Dyer, et al., *J. Appl. Phys.* 57, p. 1420, (1985).

By ablating a portion of the stent, whether ablating the entire barrier 20 or a portion thereof, ova (or sperm) are again enabled to pass through the duct 12, thus effectively reversing sterilization of the subject.

Figure 3:
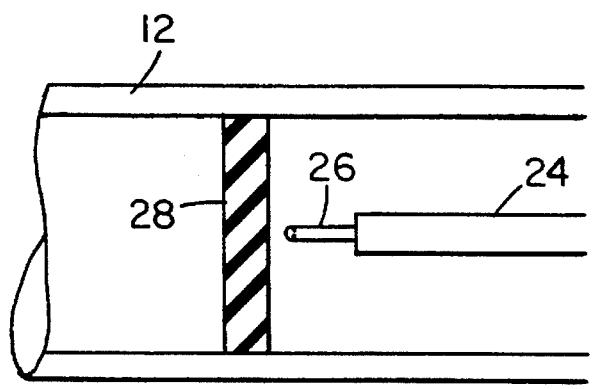
FIG. 3 is a sectional view showing an aspect of a method of the invention for reversing sterilization effected by the inventive device.

Ablation of the blocking portion of the stent 10 is achieved simply and non-surgically by inserting in duct 12 a catheter equipped with an optical fiber, typically supplied with a ball tip, by guiding the catheter to the stent and by applying laser irradiation thereto of sufficient intensity to ablate the barrier. This step of the inventive method is illustrated by drawing FIG. 3, symbolically showing a catheter 24 and an appropriately tipped optical fibre 26 applying laser radiation to an ablatable structure 28, generally representing barrier 20 of the embodiment of FIG. 1 and the corresponding portion of the embodiment of FIG. 2.

Figure 4:
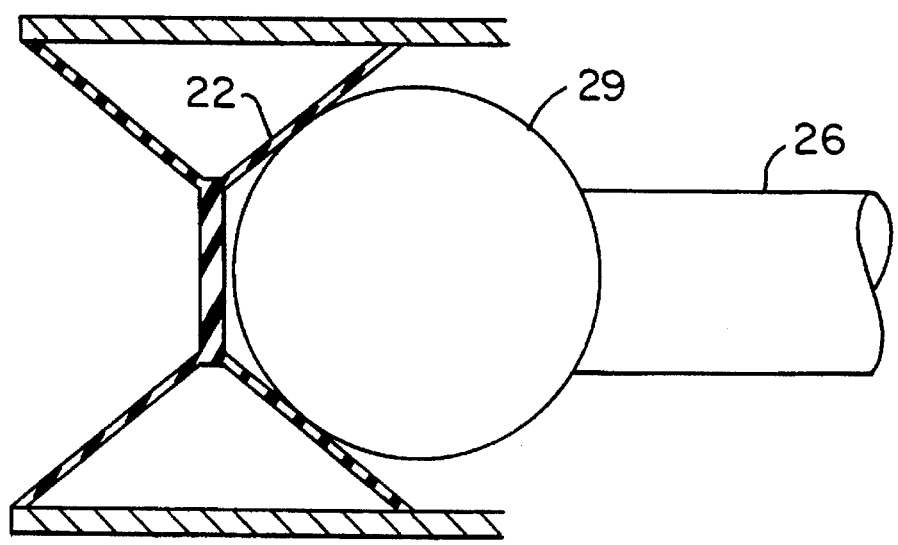
FIG. 4 illustrates a particular ball tip structure for an optical fiber as shown in FIG. 3.

Towards that end, the frustoconical shape illustrated in FIG. 1 is used to guide the optical fibre towards the ablatable portion of stent 10, thus simplifying the procedure. Moreover, by reducing the degrees of freedom of movement of the optical fiber applying the laser radiation, the frustoconical shape of the stent reduces the likelihood of damage to the patient by improperly oriented laser radiation. Still further, the funnel shape of the stent, once reopened in accordance with the invention, also aids flow or movement of sperm or ova therethrough after ablation. Preferably the fiber may have a ball shape tip for matingly docking with the conically shaped stent. Such a structure is shown in FIG. 4 wherein ball 29, which is formed of the same material as fiber 26, is guided into position by the frustoconical structure of annular portion 22, of the stent.

Of course, other shapes may be provided to the stent of FIG. 1 to achieve specific goals. For example, although FIG. 1 shows the device to have a symmetric frustoconical structure, the structures on the two sides of barrier 20 need not be the same. Thus, a specific conical angle may be chosen on one side of the barrier for guiding the laser applying optical fiber, while a different angle or a different shape may be chosen on the other side of the barrier for enhancing passage of sperm or ova therethrough. Moreover, it should be recognized that the illustrated structure shows the embodiment of FIG. 1 as being hollow in the guiding portion thereof, as being formed of a one piece polymer structure integral with the ablatable barrier 20, and as being formed of a different material from the seating element 16. However, the entire stent 10 may be a one-piece integrated device formed of one material, which may be a polymer or a polymer coated metal as hereinabove described; may be hollow or solid; and may have any combination of the above features selected for specific utilities.

Moreover, the device of the invention may be fabricated in different sizes, with an appropriate size selected to match an endoscopically determined lumen diameter for the duct or tube to be blocked. Alternatively, where a material is chosen for the seating element 16 having sufficient flexibility to assure a sealing engagement of the engaging structure 18 and the duct 12, a reduced number of sizes may be manufactured. Indeed, it may be economically advantageous to manufacture only a single size.

Figure 2:
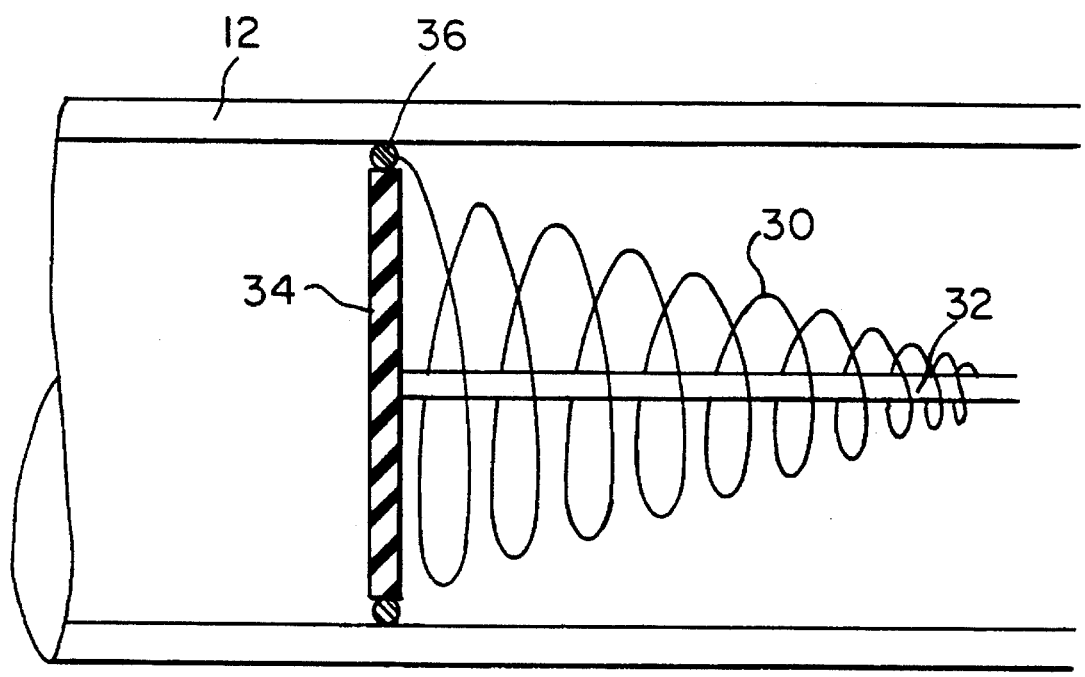
FIG. 2 is a sectional view of a second embodiment of the inventive device seated in a duct and an insertion tool therefor.

In order to facilitate such a "one-size-fits-all" device, there is illustrated in FIG. 2 an alternative embodiment of the invention.

The device shown in FIG. 2 is simpler than that shown in FIG. 1. The frustoconical guiding portion of the first embodiment is omitted, and a simpler technique may be used to expand the device and to seat the same within the duct. Specifically, the device illustrated in FIG. 2 includes a spring structure 30, a rod 32, a membrane 34 and a seating or engaging element 36. While rod 32 is shown in contact with membrane 34 of the stent, the two components of this embodiment of the invention are not attached to one another.

The seating or engaging element 36 is preferably of flexible material and is substantially annular in shape. The element may be the last coil or coils of spring 30, or may be a ring attached to the spring. Indeed, the element may be made of metal (appropriately coated as hereinabove described) or of a biocompatible material such as a biocompatible polymer. In either form, element 36 is attached to spring 30 which is used to compress the seating or engaging element.

Spring 30 is essentially cylindrical in shape, forming a known helical structure. As is known, the outer diameter of such a spring may be reduced by tightening the spring. Thus, when viewing the device along rod 32 toward membrane 34, rotation of spring 30 in the clockwise direction will result in compression thereof, and in reduction of the diameter thereof as well as of the seating or engaging element 36. Such rotation may be effected by releasably attaching a portion of spring 30, preferably the right most portion thereof in FIG. 2, to rod 32 and by rotating the rod in the clockwise direction. Upon providing the rotation element 36 will be compressed, to permit free movement of the stent within the duct 12.

Once the stent is positioned at the appropriately determined location therefor, spring 30 may be released from rod 32, thus freeing the leftmost coils thereof to expand and, therewith, to expand element 36 and to obtain appropriate sealing engagement with duct 12. Similar techniques are used in connection with coronary angioplasty procedures as hereinabove described.

In the present invention, membrane 34, which is attached to and is surrounded by element 36, similarly expands and forms the barrier within the stent ring, to effect blockage of duct 12. After expansion of element 36 rod 32 may be left in place or may be withdrawn. Similarly, spring 30 may be left in place or may be endoscopically cut, to provide future access to membrane 34 for ablation and for reopening of duct 12. Spring 30 may be formed of a polymer coated metal or may be dissolvable.

An advantage of the embodiment of FIG. 2 over that of FIG. 1 is that it is not necessary to inflate a balloon for purposes of seating the stent in Figure 2. Moreover, membrane 34 may be selected to have sufficient flexibility as to permit expansion of the stent to fit a large range of sizes of ducts or tubes of a human reproductive system.

Restoration of fertility may be effected in the same manner as hereinabove described for the embodiment of FIG. 1. Upon reference to FIG. 3, ablatable structure 28 is seen to represent membrane 34, or a predetermined ablatable portion thereof. Application of a laser beam thereto thus reopens the duct and reestablishes fertility of the subject.

In order to aid compatibility of the inventive devices with the living tissue to which the devices are exposed, and to prevent infection in the subject, it is contemplated to incorporate an antibiotic or the like in the polymer, for slow release. The antibiotic would be compatible with the reproductive system or with other elements of the body exposed thereto. Such techniques have been successfully implemented in implant devices.

Accordingly, there has been described a method and device for reversibly blocking a duct or a tube, and more specifically for reversibly blocking a duct in the human reproductive system thus reversibly sterilizing a human subject. The devices have no moving parts, are easily and inexpensively manufactured, are non surgically implanted and non surgically ablated, and provide an effective means for reversibly sterilizing human subjects.

The foregoing description of the preferred embodiments of the invention has been presented for purposes of illustration and description. It is not intended to be exhaustive or to limit the invention to the precise forms disclosed since many modifications or variations thereof are possible in light of the above teaching. For example, different shapes may be used to attain further advantages of the inventive concept. Different materials may be used to fabricate the device, different devices and techniques may be used to insert and position the stent, and different devices and techniques may become available for ablating, vaporizing, liquefying, or otherwise eliminating the barrier portion of a stent. All such modifications are within the scope of the invention. The embodiments described herein were chosen and described in order best to explain the principles of the invention and its practical application, thereby to enable one of ordinary skill in the art to utilize the invention in various embodiments and with various modifications as are suited to the particular use contemplated therefor. It is intended that the scope of the invention be defined by the claims appended hereto, when interpreted in accordance with full breadth to which they are legally and equitably entitled.

I claim:

1. A method of reversible sterilization of a subject, comprising the steps of:
   inserting a blocking member into a duct in a reproductive system of the subject thereby to block the duct; and
   changing dimensions of an engaging element of the blocking member thereby to engage the duct and to seal the blocking member in the duct further comprising the steps of:
   inserting an optical device into the duct; and
   applying laser irradiation to the optical device thereby to ablate a predetermined portion of the blocking member and to unblock the duct.

2. The method of reversible sterilization recited in claim 1 wherein said step of changing dimensions comprises enlarging an outer dimension of the engaging element in order to engage an inner surface of the duct.

3. A method of reversible sterilization of a subject, comprising the steps of:
   inserting a blocking member into a duct in a reproductive system of the subject thereby to block the duct; and
   changing dimensions of an engaging element of the blocking member thereby to engage the duct and to seal the blocking member in the duct,
   wherein said step of inserting comprises inserting into the duct a stent including said blocking member centrally located therein and including said engaging element at a peripheral portion thereof, and
   wherein said step of changing dimensions comprises the steps of endoscopically inserting a balloon structure at a distal end of a catheter to a vicinity of said engaging element and enlarging said balloon structure to contact and enlarge said engaging element thereby to cause said engaging element to expand and sealingly engage an inner surface of the duct.

4. A method of reversible sterilization of a subject, comprising the step of:
   inserting a blocking member into a duct in a reproductive system of the subject thereby to block the duct; and
   changing dimensions of an engaging element of the blocking member thereby to engage the duct and to seal the blocking member in the duct,
   wherein said step of inserting comprises inserting into the duct a compressed stent including said blocking member centrally located therein and including said engaging element at a peripheral portion thereof, and
   wherein said step of changing dimensions comprises the step of releasing a spring means compressing said stent thereby enlarging said peripherally located engaging element to contact and sealingly engage an inner surface of the duct.

5. In a method for sterilizing a reproductive system by using a blocking device for blocking a duct therein, the improvement comprising:
   reversing the sterilization effected by the blocking device;
   said reversing step comprising the step of thermally ablating a portion of the blocking device thereby to reopen the duct.

6. The improved sterilization method recited in claim 5, wherein said step of thermally ablating comprises applying laser radiation to the blocking device.

7. The improved sterilization method recited in claim 5, wherein said step of thermally ablating comprises the further steps of:
   positioning an optical device adjacent the blocking device in the blocked duct; and
   applying a predetermined intensity of laser radiation to the optical device for ablating said portion of the blocking device.

8. Apparatus for reversibly blocking a duct in a reproductive system comprising, in combination:
   a laser beam reversible blocking device;
   said blocking device including:
      seating means for seating the device in the duct, and
      blocking means for blocking passage of reproductive gametes therethrough;
      wherein said blocking means includes an abalatable portion of a material suitable for abalation by a laser beam, said ablatable portion having a predetermined thickness such that the ablatable portion is ablated by application of an ablating laser beam thereto;
   the apparatus further including, in combination with said blocking device, first guide means guiding an ablating laser beam to said ablatable portion of said blocking means, thereby to apply an ablating laser beam thereto.

9. The apparatus recited in claim 8, wherein said blocking device further comprises a stent including said seating means at a peripheral portion thereof, wherein said ablatable portion of said blocking means is mounted to said seating means and is located substantially at a central portion of said stent.

10. The apparatus recited in claim 7 wherein said seating means comprises a flexible portion adapted to be flexibly enlarged by application of pressure thereto and means for engaging an inner surface of the duct, and
   said blocking device further comprises second guide means connecting said ablatable portion to said seating means of said stent for guiding a distal end of a catheter to contact said ablatable portion to apply said ablating laser beam thereto.

11. The reversible blocking device recited in claim 9 wherein said seating means comprises a coiled annular portion adapted to be flexibly enlarged by application of spring pressure thereto, and
   further comprising spring means for releasably compressing said annular portion of said stent during insertion in the duct;
   said spring means engaging said annular portion and, upon release of said spring means, enlarging said annular portion of said stent to engage the duct.

12. The reversible blocking device recited in claim 8, wherein said ablatable portion of said blocking means comprises a membrane having a thickness in the range of 0.1 mm to 3 mm.

13. The reversible blocking device recited in claim 8, wherein said membrane has a thickness in the range of 0.5 mm to 1 mm.

14. The reversible blocking device recited in claim 8, wherein said ablatable portion comprises a material susceptible to ablation by a laser beam having an intensity of approximately 1 J/cm$^2$.

15. The reversible blocking device recited in claim 14, wherein said ablatable portion of said blocking means comprises a membrane having a thickness in the range of 0.1 mm to 3 mm.

16. The reversible blocking device recited in claim 15, wherein said membrane has a thickness in the range of 0.5 mm to 1 mm.

17. The method of reversible sterilization of a subject recited in claim 1, wherein said step of inserting a blocking member comprises inserting the blocking member non-surgically in a natural opening of the duct in the reproductive system of the subject.

18. The method of reversible sterilization of a subject recited in claim 5, wherein said step of thermally ablating a portion of the blocking device comprises non-surgically inserting an ablating means in a natural opening of the duct in the reproductive system.

* * * * *